(12) United States Patent
Chung et al.

(10) Patent No.: US 10,107,805 B2
(45) Date of Patent: Oct. 23, 2018

(54) VIRUS-MICROBEAD COMPLEX AND USE THEREOF

(71) Applicant: SEOUL NATIONAL UNIVERSITY R&DB FOUNDATION, Seoul (KR)

(72) Inventors: Taek Dong Chung, Gwacheon-si (KR); Inseong Hwang, Seoul (KR); Chang Su Jeon, Yeosu-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 197 days.

(21) Appl. No.: 14/758,126

(22) PCT Filed: Sep. 2, 2013

(86) PCT No.: PCT/KR2013/007903
§ 371 (c)(1),
(2) Date: Jun. 26, 2015

(87) PCT Pub. No.: WO2014/104534
PCT Pub. Date: Jul. 3, 2014

(65) Prior Publication Data
US 2016/0054314 A1    Feb. 25, 2016

(30) Foreign Application Priority Data
Dec. 28, 2012 (KR) .................... 10-2012-0157524

(51) Int. Cl.
G01N 33/543      (2006.01)
G01N 33/554      (2006.01)
G01N 33/553      (2006.01)

(52) U.S. Cl.
CPC ... G01N 33/54333 (2013.01); G01N 33/5432 (2013.01); G01N 33/553 (2013.01); G01N 33/554 (2013.01); G01N 2333/005 (2013.01)

(58) Field of Classification Search
None
See application file for complete search history.

(56) References Cited

PUBLICATIONS

Xie et al., Langmuir 2011 vol. 11, pp. 11394-11400.*
Muzzard et al. small 2012 vol. 8, pp. 2403-2411.*
Liu et al., Chem Soc Rev 2012, vol. 41, pp. 6178-6194.*
Parkhouse et al. Bioorganic & Medicinal Chemistry 16 (2008) 6641-6650.*
Ghosh et al., "M13-templated magnetic nanoparticles for targeted in vivo imaging of prostate cancer," Nature Nanotechnology 7:677-682 (Oct. 2012).
Jeon et al., "Virus-tethered Magnetic Gold Microspheres with Biomimetic Architectures for Enhanced Immunoassay," The Korean Chemical Society (3 pages) (Oct. 17, 2012).
Jeon et al., "Virus-Tethered Magnetic Gold Microspheres with Biomimetic Architectures for Enhanced Immunoassays," Advanced Functional Materials, doi: 10.1002/adfm.201202499 (13 pages) (Oct. 26, 2012).
Khalil et al., "Single M13 bacteriophage tethering and stretching," PNAS 104(12):4892-4897 (Mar. 20, 2007).
Liu et al., "Natural supramolecular building blocks: from virus coat proteins to viral nanoparticles," Chem. Soc. Rev. 41:6178-6194 (2012).
Muzard et al., "M13 Bacteriophage-Activated Superparamagnetic Beads for Affinity Separation," small 8(15):2403-2411 (2012).

* cited by examiner

Primary Examiner — Shanon A. Foley
Assistant Examiner — Myron G Hill
(74) Attorney, Agent, or Firm — Seed IP Law Group LLP

(57) ABSTRACT

The present invention relates to a virus-microbead complex including a microbead and a virus layer, in which linear viruses are bound individually to the surface of the microbead, and an immunoassay kit including the same.

The virus-microbead complex of the present invention is characterized in that the linear viruses are bound to the surface of the microbead so that the orientations of the linear viruses are regulated using the interaction of streptavidin-biotin introduced thereon, thereby providing a significantly increased volume to surface area ratio, increasing the number of antibodies or ligands capable of binding thereto, and as a result, mediating the binding of antibodies or ligands to a unit bead with high density, which eventually leads to an increased sensitivity in immunoassays, and an application into a suspension array. Additionally, it was confirmed that cardiac troponin I (cTnI) in serum can be detected up to 20 pg/mL by introducing a self-assembled monolayer (SAM) containing PEG to remove a non-specific adsorption.

14 Claims, 8 Drawing Sheets
Specification includes a Sequence Listing.

(a)

(b)

SEQUENCE LISTING

<160> NUMBER OF SEQ ID NOS: 3

<210> SEQ ID NO 1
<211> LENGTH: 67
<212> TYPE: DNA
<213> ORGANISM: Artificial Sequence
<220> FEATURE:
<223> OTHER INFORMATION: Primer AP-F

<400> SEQUENCE: 1
cggccatggc aggtctgaac gacatcttcg aggctcagaa aatcgaatgg cacgaaggct     60
ccggtgc                                                              67

<210> SEQ ID NO 2
<211> LENGTH: 74
<212> TYPE: DNA
<213> ORGANISM: Artificial Sequence
<220> FEATURE:
<223> OTHER INFORMATION: Primer AP-R

<400> SEQUENCE: 2
ggccgcaccg gagccttcgt gccattcgat tttctgagcc tcgaagatgt cgttcagacc     60

```
tgccatggcc ggct                                                         74

<210> SEQ ID NO 3
<211> LENGTH: 15
<212> TYPE: PRT
<213> ORGANISM: Artificial Sequence
<220> FEATURE:
<223> OTHER INFORMATION: Acceptor peptide

<400> SEQUENCE: 3

Gly Leu Asn Asp Ile Phe Glu Ala Gln Lys Ile Glu Trp His Glu
1               5                   10                  15
```

VIRUS-MICROBEAD COMPLEX AND USE THEREOF

CROSS-REFERENCE TO RELATED APPLICATION

This application claims priority to and the benefit of Korean Patent Application No. 10-2012-0157524, filed Dec. 28, 2012, the disclosure of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860175.407USPC_SEQUENCE_LISTING.txt. The text file is 1.2 KB, was created on Oct. 15, 2015, and is being submitted electronically via EFS-Web.

BACKGROUND

Technical Field

The present invention relates to a virus-microbead complex including a microbead and a virus layer, in which linear viruses are bound to the surface of the microbead, and an immunoassay kit including the same.

Description of the Related Art

Recently, it has been proven that viruses are recognized as a useful tool in detecting a target analyte such as explosive substances, proteins, bacteria, viruses, spores, and toxic substances with high selectivity and sensitivity. Among bacteriophages (hereinafter, abbreviated as a phage), viruses responsible for specifically infecting a bacterium, a target-specific insoluble phage may be identified by a stable phage-display technique, whereas a soluble phage releases a cell-specific marker molecule such as an enzyme, which is analyzable, by specifically destroying a bacterium, and thus the virus is among the most extensively studied. Moreover, a phage having a superior chemical and thermal stability may bind to a nano or microstructure, and may be fixed to the surface of a converter of an analyzer.

Recently, the emergence of those virus-based mixed materials enables the implementation of highly selective and highly sensitive biosensors. The advantages of a complex consisting of a virion and biosensing material are intuitively derived from the innate physical properties resulted from the molecular recognition ability of the virion and the form of a phenotype. However, a detection system still remains in a 2D-flat platform and that it needs relatively large amount of analytes and analytical time, despite the functional advantages of the biosensors that use virus-mixed materials.

A linear bacteriophage such as Fd and M13 is in the form of a nano structure having a length of about 1 μm and a diameter of about 7 nm. The virus is composed of five different types of structural proteins (pIII, pVI, pVII, pVIII, and pIX) encapsulating a single-stranded viral DNA. Among the structural proteins, more than 2700 copies of major coat protein pVIII may be applied as a linear-structured assembly having an ε-amino group on Lys-8 and an α-amino group exposed at N-terminal, which may be successfully modified into a macromolecule using a chemical bonding, respectively. pIII, a secondary coat protein having 3 to 5 copies per each virion, is mainly used in a peptide and protein display (FIG. 1).

Meanwhile, due to the recent development of a microstructure manufacturing technique, nano or microstructures have been explicitly used for a great number of analyses. Accordingly, this has led to the formation of a microstructure made of various materials, and methods for modifying the microstructure and introducing the microstructure into other materials are continuously being studied, and as a result, desired results have been achieved. However, due to the nature of the materials, a non-specific adsorption of polymer beads, which are used extensively in general, is inevitable. Specifically, micro-sized structures are currently applied for immunoassays, etc., by binding of a molecule capable of specifically capturing an analyte, such as an antibody, to the surface of the structure. However, when the micro-sized structures are applied for separating an analyte from a sample containing various proteins such as serum, it not only captures an antibody-specific analyte bound to a bead, but also plays a key role in decreasing analysis sensitivity by increasing the background signal with an adsorption of other proteins to the surface of the bead. Accordingly, in order to employ those microstructures for immunoassays such as a serum analyte, there is a need for a solution to prevent non-specific bindings.

The foregoing discussion in this section is to provide general background information, and does not constitute an admission of prior art.

SUMMARY

One objective of the present invention is to provide a virus-microbead complex including a microbead and a virus layer, in which one end of each linear virus is bound to the surface of the microbead.

Another objective of the present invention is to provide an immunoassay kit including the virus-microbead complex.

The virus-microbead complex of the present invention has an advantage in that the linear viruses are bound to the surface of the microbead so that the orientations of the linear viruses are regulated using the interaction of streptavidin-biotin introduced thereon, thereby providing a significantly increased volume to surface area ratio, increasing the number of antibodies or ligands capable of binding thereto, and as a result, mediating the binding of antibodies or ligands to a unit bead with high density, which eventually leads to an increased sensitivity in immunoassays, and an application into a suspension array. Additionally, it was confirmed that cardiac troponin I (cTnI) in serum can be detected up to 20 pg/mL by introducing a self-assembled monolayer (SAM) containing PEG to remove a non-specific adsorption.

DESCRIPTION OF EMBODIMENTS

In a first aspect, the present invention provides a virus-microbead complex including a microbead and a virus layer, in which one end of each linear virus is bound to the surface of the microbead.

The shape of a linear virus membrane provides an opportunity for the virus to construct a bioinspired architecture that regulates various cell functions via a cellular threadlike structure. Further, a long, flexible tether and polyvalency may provide a proper function during a biological recognition process such as a ligand-receptor interaction.

In order to apply such structural features of the linear virus to an immunoassay kit, the present invention is characterized by binding of one end of each linear virus to a microbead to expose the long axis of the linear viruses, thereby enabling the binding of a capturer for capturing an analyte to the long axis of the linear virus with high density.

Herein, the linear viruses bound to the surface of the microbead may be separated from each other by adjusting the orientation in such a way that one end of each individual linear virus is independently bound to the microbead.

Generally, a "virus" refers to a small infectious material capable of replicating only inside the living cell of an organism, and is able to infect all types of organisms, that is, from animals to bacteria and archaea. The virus particles (virions) consist of two or three parts: i) the genetic material made of DNA or RNA, long molecules that carry genetic information, ii) a protein coat that protects the genes, and in some cases, an envelope of lipids that surrounds the protein coat when they are outside a cell. The shape of viruses includes linear (helical rod), icosahedrons, or expanded icosahedrons forms, and the average size of the viruses is about 1/100 the size of the average bacterium. Preferably, the virus of the present invention is a specific-virus, that is, a "bacteriophage", a virus that specifically infects and replicates within a bacterium, and is abbreviated as "phage". A phage may be divided into lytic and nonlytic. Preferably, the phage of the present invention may be nonlytic, and more preferably, the non-limiting examples of the linear virus include fd or M13 phage, etc. These phages take a linear structure of a rod shape having a long axis of about 1 μm and a diameter of about 7 nm. The nonlytic phage does not destroy a host cell when it infects the host cell. The genome of the phage is integrated into the host DNA to be replicated, which is known as lysogeny. In this condition, the host cell continues to live and reproduce, and the phage also reproduces and amplifies.

Such virus may be applied to a biosensor, etc., due to its morphological features and the possibility of site-specific gene modification, etc. That is, the linear virus has an advantage in that it may provide an increased potential interaction surface due to a high surface area to volume ratio as one of morphological features. Meanwhile, the site-specific gene modification enables to express a specific protein or peptide on the surface.

A filamentous M13 or fd phage is characterized in that about 3000 copies of pVIII major coat protein, encapsulates the ring-shaped single-stranded DNA genome, and 3 to 5 copies of pIII, pVI, pVII, or pIX, which are proteins with different structures, may be present at its both ends. Alternatively, by introducing a gene coating a foreign protein into the single-stranded genome via a gene-manipulation, the phage may further be manipulated to express the DNA genome at desired sites.

The virus layer according to the present invention is formed by binding between one end of each linear virus and the surface of a microbead, and thus, preferably, the orientation may be regulated. In order to regulate the orientation of the viruses that bind to the surface of the microbed, the interaction between streptavidin (SAV) and biotin may be employed. For example, SAV may be introduced onto the surface of the microbead, and the viruses may be modified for enabling one end of each virus, that is, pIII, to bind to the microbead. The biotin may be expressed by a gene-manipulated virus, in which the virus itself expresses biotin at one end of pIII via a gene manipulation, or may be used by preparing from outside and binding to pIII using a method known in the art.

The virus layer formed by binding between one end of each virus and the surface of the microbead, in which the orientation of the viruses are regulated, according to the present invention, may provide an increased surface area by exposing the surface of the long axis of the virus. The surface of the long axis includes thousands of copies of pVIII coat protein, and the coat protein includes Ala and Lys residues, which are easily modified by phosphine group exposed to the outside, thus providing the potential to introduce an increased number of functional molecules.

A capturer for immunoassay may bind to the functional molecules introduced into the exposed long axis surface of the virus. The non-limiting examples of the capturer include an antibody, an antigen, a ligand, a receptor, or a combination thereof. Preferably the binding between the virus and capturer may be achieved via a covalent bond providing a strong binding capacity.

The term "microbead" used herein may be a microbead having an average diameter ranging from 0.5 to 500 μm, and preferably, may be in the form of a uniform spherical particle. The microbead may separate biological substances, such as cells, proteins, or hexanes, by adsorbing or binding of a biologically reactive molecule to the surface of the microbead. The microbead of the present invention includes "a microsphere." The microbead may be prepared from various materials including natural products, compounds, metals, glasses, polymers, and ceramics, etc., and a variety of products are commercially available. Further, the microbead may include not only closely packed beads but also hollow microspheres, and this would mean that any of the beads can be provided as a particle of varying density even if it is made of the same materials. Since one of ordinary skill in the art may use methods known in the art, without limits, to modify the surface of the microbead, other functional groups or materials may be easily introduced. In addition, particles having a further special feature such as a magnetic property may be used depending on the purpose.

Meanwhile, the microbead used in the virus-bead complex of the present invention may be made of gold with high reactivity or coated with a thin gold film, to facilitate the modification of the surface of the microbead. Specifically, since gold has a high reactivity with a thiol group, if a microbead having a gold surface, that is, either made of gold or coated with a thin gold film although made of a different material, is used, the microbead will be readily bound to a molecule containing thiol group.

The microbead used in the virus-bead complex of the present invention preferably includes a self-assembled monolayer (SAM), which is further formed on the surface of the microbead for preventing a non-specific binding. The SAM may consist of molecules containing polyethylene glycol. The non-limiting examples of the molecule include carboxyl-terminated hexa(ethylene glycol)undecane thiol. The further formed SAM prevents a non-specific binding of an undesirable protein, etc., to the surface of the microbead, and subsequently, the non-specifically bound materials increase the background signal, thereby preventing the inhibition of a sensitivity analysis of trace amount of a target material. Preferably, the molecule may contain a thiol group at one end to bind to the gold surface of the microbead, thereby forming a SAM, and the non-specific binding between the molecule and the surface of the microbead may be prevented as the molecule contains ethylene glycol group. On the other hand, different functional molecules may further be easily introduced as the molecule contains carboxyl group at another end. Specifically, the molecule may react with 1-ethyl-3-(3-dimethylaminopyl)-1-carbodiimide hydrochloride (EDC) and N-hydroxysuccinimide (NHS) sequentially followed by a reaction with streptavidin or biotin to provide a microbead, incorporated with streptavidin or biotin by a strong peptide bond on the surface of the microbead, thus facilitating the binding between the microbead and the linear virus modified with biotin or streptavidin at one end.

In the present invention, the binding between the microbead and the linear virus is preferably mediated by the binding between streptavidin (SAV) and biotin.

By such binding, the virus-microbead complex of the present invention may include a SAM on the surface, and streptavidin or biotin may be bound to its outside.

As described above, the linear virus may be fd or M13 phage, more preferably, the biotin or streptavidin is bound to a protein located at one end of the virus, or the virus is gene-manipulated to express a fusion protein of biotin or streptavidin and a virus protein. The one end refers to at least one end, and thus the binding between biotin or streptavidin and the protein located at both ends of the virus, or expressing biotin or streptavidin via a gene-manipulation is included within the scope of the present invention. In one embodiment of the present invention, the protein located at one end of the virus is pIII, pVI, pVII, pIX, or a combination thereof.

Further, for the purpose of an easy separation of an analyte from a mixed sample in addition to analysis, the microbead may be magnetic. For example, when the microbead is magnetic, the analyte bound to the complex of the present invention may be easily separated from the mixed sample by providing a strong external magnetic field using a magnetic property, and further, the analyte may be recovered by separating it from a capturer by a method known in the art, as needed.

In a second aspect, the present invention provides an immunoassay kit including the virus-microbead complex according to the present invention.

Generally, an immunoassay refers to a biochemical test that measures the presence or concentration of a macromolecule in a solution using an antibody or immunoglobulin. The macromolecule detected by the immunoassay is often referred to as an analyte and is in many cases a protein. Biological liquids such as serum or urine are frequently measured as analytes via immunoassays for medical and research purposes. However, in the present invention, an "immunoassay" may include not only an analysis of a specific antigen-antibody binding using the antibody or immunoglobulin but also an analysis of a receptor or ligand using a specific receptor-ligand binding. For example, the immunoassay of the present invention may detect an analyte that can specifically bind to the capturer bound to the virus of the virus-microbead complex. The capturer may be an antibody, an antigen, a ligand, a receptor, or a combination thereof, as described above. Also, an analyte that can be detected thereby may be an antigen, an antibody, a receptor, a ligand, or a combination thereof that can specifically bind thereto, respectively. That is, the virus-microbead bound to an antibody as a capturer may be used in detecting the antigen that specifically binds thereto. Inversely, the virus-microbead bound to an antigen may be used in detecting the antibody that specifically binds thereto. Similarly, the complex bound to a ligand as a capturer may be used in detecting the receptor bound thereto, and the complex bound to a receptor as a capturer may be used in detecting the ligand bound thereto.

A conventional immunoassay kit is equipped with an antibody, a reaction buffer solution, and a labeling material that can bind specifically to an analyte. The antibody is present in a floating state in a solution or in a state of being fixed to a plate for detection. Specifically, in the case of detecting a trace amount of an analyte, an analysis of the antibody in a solution may be conducted using the volume of a container or by fixing the antibody on a narrow area of the plate.

The immunoassay kit may comprise the complex according to the present invention; and further a capturer for capturing an analyte, which is bindable to the surface of the virus within the complex. Also, it may further include a labeling material for detection.

The virus and the capturer capable of capturing analyte are the same as defined above, and the capturer may bind to the surface of the virus by a non-limiting binding method. The capturer may directly or indirectly bind to the surface of the virus. For example, the capturer may directly bind to the outside of pVIII, a protein encapsulating the long axis, using a gene-manipulated virus so that a protein that can specifically bind to the capturer is expressed, and the capturer may bind to an amino acid residue exposed to the outside of the protein by modifying a molecule or protein having superior reactivity via the same. Preferably, the capturer may be linked to the surface of the virus via a covalent bond. The term "covalent bond" used herein refers to a chemical bond that involves the sharing of electron pairs between atoms, and a stable balance of attractive and repulsive forces exists between the atoms. The covalent bond provides a stable chemical bond withstanding an injection of a sample and washing thereof by providing a much stronger binding capacity compared to that of van der Waal's interaction, a hydrogen bond, or a non-covalent bond.

Preferably, the covalent bond may be achieved by Staudinger ligation. In this regard, in an exemplary embodiment of the present invention, a phosphine group was introduced into an Ala or Lys residue located at N-terminal of the coat protein exposed to the surface of the virus, and the antibody for capturing a material to be analyzed was modified with azide, and linked to the phosphine group by a covalent bond.

The immunoassay kit according to the present invention may use any labeling materials as a labelling material and detection methods generally used in immunoassays, without limits. A capturer to which a labeling material that is chemically bonded or conjugated, or any separate antigen, antibody, etc., to which the labeling material is chemically bonded or conjugated may be detected by binding them through a further reaction after they are reacted with an analyte. For example, the labeled materials may be an enzyme, radio isotope, a fluorescent substance, an adsorbing substance, and a luminous substance, etc., and a separate labeling material may not be needed depending on a detection method to be used. The non-limiting examples of the detection methods may include absorbance measurement, fluorescence or luminescence measurement, surface Plasmon resonance, and electrochemical impedance spectroscopy, etc.

The term "suspension array" used herein refers to a method used in detecting a high throughput, large-scale, and multi-screening in molecular biology, and has been widely applied to genomic and proteomic research. Specifically, it is a method of analysis employing the microbead having a diameter of several micrometers and the same principle as in the immunoassays, and is used for simultaneously classifying and/or analyzing a plurality of analytes in a floating or liquid state, which are labeled with different labeling materials. The representative example of the suspension array may be a cell classification via flow cytometry. As such, for suspension array, the sensitivity of a detector must be very high, or a bead must contain a sufficient amount of labeling materials to enable the detection of an individual bead.

In a general immunoassay, an antigen binds to an antibody in a 1:1 ratio, and thus, the detection is mostly conducted by reacting a sample with an antibody fixed on the plate because it is difficult to detect an antigen in a floating or liquid state despite using a labeling material. However, the virus-microbead complex of the present invention is characterized in that a plurality of linear viruses with regulated orientation, are bound to the surface of the microbead, and each linear virus includes on the surface a coat protein, in which the amino acid residues, which are capable of introducing a material (e.g., an antibody) that specifically binds to a analyte, are exposed on the surface of the protein, thereby enabling a binding of a significantly increased number of antibodies per each bead, which increases immunoassay sensitivity. Accordingly, the virus-microbead complex may be used in a suspension array even when an antigen is in a floating or liquid state.

When the microbead has a magnetic property, the analyte may be separated by separating the analyte-bound complex using the magnetic property. For example, among the mixed analytes, the analyte bound within the complex of the present invention may be easily separated by providing a strong external magnetic field using magnetic property, and further, the analyte may be recovered by separating it from the capturer by a method known in the art, as needed.

MODE FOR INVENTION

Figure 1:
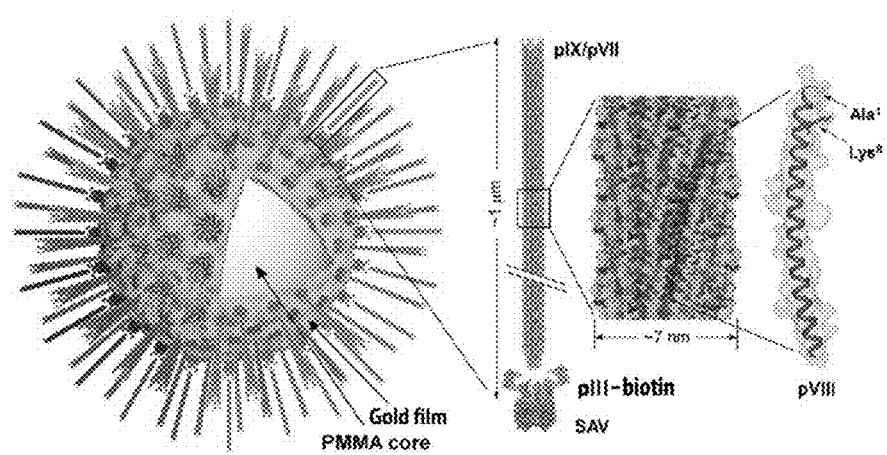
FIG. 1 is a schematic diagram illustrating a composition of a virus-microbead complex according to the present invention. The thin gold film on the microbead facilitates a surface modification by thiol SAM leading to a subsequent chemical bonding of a functional protein such as SAV (purple). The SAV-modified microbead is modified with a linear structural pIII-biotinylated phage virion (light blue) to have a surface similar to the shape of a particular cell. The amine group exposed to the surface of Ala-1 (yellow rod) and Lys-8 (red rod) at N-terminal of the main coat protein of the virus (individual pVIII units are illustrated in blue) binds to a primary antibody by Staudinger ligation to provide an antibody-bound microbead with high density. The shape of the protein was formed using VMD based on PDB code 1IFJ.

Hereinafter, the present invention will be described in more detail with reference to the following examples. However, the following examples are provided for illustrative purposes only, and the scope of the present invention should not be limited thereto in any manner.

<Example 1> Reagents

Sulfo-N-hydroxysulfosuccinimide (sulfo-NHS), sulfo-NHS-phosphine, NHS-PEG$_{12}$-azide, and 1-ethyl-3[3-dimethylaminopropyl]carbodiimide hydrochloride (EDC) were purchased from Thermo Scientific (Rockford, Ill., USA). Carboxyl-terminated hexa(ethylene glycol) undecane thiol (CMT002) was purchased from Nanoscience Instruments (Phoenix, Ariz., USA). Carbenicillin (Carb) and isopropyl β-D-1-thiogalactopyranoside (IPTG) were purchased from Gold Biotechnology (St. Louis, Mo., USA). Streptavidin (SAV), bovine serum albumin (BSA), tetracycline (tet), tween-20, adenosine-5-triphosphate (ATP), and cardiac troponin I (cTnI) were purchased from Sigma-Aldrich (St. Louis, Mo., USA). A plasmid pET21a-BirA was purchased from Addgene (Cambridge, Mass., USA). Magnetic gold-microbeads (M-NG0501, Nomadien.com) were prepared by a proprietary method containing electroless plating of auric acid on a proprietary magnetic poly(methyl methacrylate) (PMMA) bead (Nomadien.com) having a diameter of 15 μm. Carboxylated polystyrene (PS) beads having a diameter of 10 μm were purchased from Polysciences (Warrington, Pa., USA). Phage vectors, fd-tet having SfiI and NotI restriction sites in front of pIII, were provided by Philip Holliger and Dr. Changhun Nam. Rabbit polyclonal anti-fd (ab6188) and anti-cTnI (ab47003) antibodies were purchased from Abcam (Cambridge, Mass., USA). Mouse monoclonal anti-cTnI antibodies [19C7] were purchased from GeneTex (Irvine, Calif., USA). Chicken alexa fluor 594 anti-mouse antibodies (A21201), goat alexa fluor 610-R-phycoerythrin (PE) anti-rabbit antibodies, alexa fluor 594 biotin, streptavidin conjugated with horseradish peroxidase (SAV-HRP), biotin, and bacteria cell strains for a protein expression and phage amplification were purchased from Invitrogen (Carlsbad, Calif., USA). Myoglobin, rabbit polyclonal anti-myoglobin antibodies (70-MR13), and mouse monoclonal anti-myoglobin antibodies (10-M50A) were purchased from Fitzgerald (North Acton, Mass., USA).

<Example 2> Fluorescence Microscope

A gold-microbead suspended in 5 μl of phosphate buffered saline (PBS) was dropped onto a glass slide. Fluorescence was monitored using an Olympus IX71 (Olympus, Japan). Mean fluorescence intensity (MB) was determined based on at least 10 microbeads selected thereof using MS-Elements software version 2.30 (Nikon, Japan).

<Example 3> Field-Emission Scanning Electron Microscopy (FE-SEM)

The surface shape of the gold microbead on top of carbon tape was monitored using a JSM 5410LV (JEOL, Japan) having 2 kV of acceleration voltage, from National Instrumentation Center for Environmental Management of Seoul National University. In order to monitor the surface shape of the thiol SAM, SAV- and phage virion-modified gold microbeads, platinum (Pt) was sputtered at 15 mA for 100 seconds using a BAL-TEC SCD 005 sputter coater.

<Example 4> Preparation of a BirA

A His-tag BirA was prepared according to the protocol provided by applying conditional modifications. Specifically, a pET21a-BirA plasmid was transformed to *E. coli* BL21(DE3)pLysS aliquoted in a lysogeny broth-agar (LB-agar) containing 100 μg/ml of Carb. A single colony was inoculated on LB-Carb medium so that it grew until a cell density reached a mid-log phase. Herein, 10 mM of IPTG was added for induction. After incubating the single colony over night at 37° C., the cells were collected, grounded with sound wave, and centrifuged. A supernatant was loaded onto Ni-NTA column to purify BirA. A small preliminary experiment was performed using seven individual colonies, and the colony exhibiting the best expression was used in a mass-production of enzymes.

<Example 5> Preparation of Phages Containing Biotinylated Motifs

Two primers, AP-F(5'-CGG CCA TGG CAG GTC TGA ACG ACA TCT TCG AGG CTC AGA AAA TCG AAT GGC ACG AAG GCT CCG GTG C-3; SEQ ID NO: 1) and AP-R(5'-GGC CGC ACC GGA GCC TTC GTG CCA TTC GAT TTT CTG AGC CTC GAA GAT GTC GTT CAG ACC TGC CAT GGC CGG CT-3; SEQ ID NO: 2), were annealed and ligated with a fd-phage decomposed with SfiI and NotI. After confirming the ligation via a DNA sequence analysis, the phage vector was transformed into *E. coli* TG1, and the transformant was grown in an LB-agar plate containing 40 g/ml of Tet at 37° C. for 16 hours. The next morning, a single colony was selected and inoculated to a NZY liquid medium containing 3 ml of Tet (20 μg/ml) as a starter culture. For a mass production of phages, the starter culture was inoculated with 400 ml of NZY-Tet medium and grown at 37° C. for 16 hours while stirring vigorously. The phages were then purified by a precipitation of polyethylene glycol (PEG)/NaCl according to the standard protocol.

<Example 6> Biotinylation of the Phages

The purified phage virions ($10^{13}$) were incubated with BirA (30 nM), biotin (100 μM), and ATP (1 mM) in PBS-Mg (pH 7.4, 5 mM MgCl2) solution at 37° C. for 2 hours. The phages were then precipitated by PEG/NaCl, and the remaining PEG/NaCl molecules were removed by a buffer solution exchange using a Centricon (MWCO=100 kDa). The degree of biotinylation was confirmed via western blot using SAV-HRP.

<Example 7> Preparation of a Virus-Microbead Complex

Figure 2:
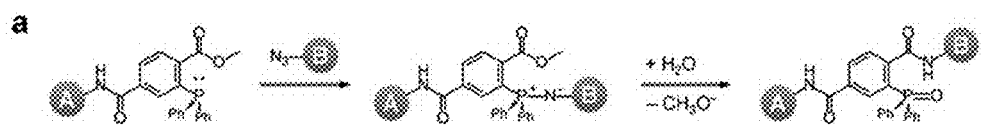
FIG. 2 is a schematic diagram illustrating a process of manufacturing the virus-microbead complex according to the present invention. (a) represents a Staudinger ligation (azide-phosphine binding) between a phosphine-activated A and an azide-labeled B. An aza-ylide intermediate (middle) is transformed into a stable covalent amide bond (right). (b) represents the formation of the virus layer from thiol SAM on the thin gold film of the microbead and the binding process of an antibody to the virus layer. First, SAM layer is introduced onto the thin gold film by a thiol group, and SAV binds to the SAM layer by a chemical conjugation. Through SAV, one end of the biotinylated linear virus, i.e., pIII, is bound to the microbead. The amine group exposed to the surface of N-terminal of the coat protein coating the long axis of the virus having such a binding, binds to phosphine, and when an azide-modified primary antibody is mixed thereto, the antibody further binds to the microbead by Staudinger ligation, thereby providing an antibody-bound microbead with high density (the ratio is different from the actual ratio).
Figure 2:
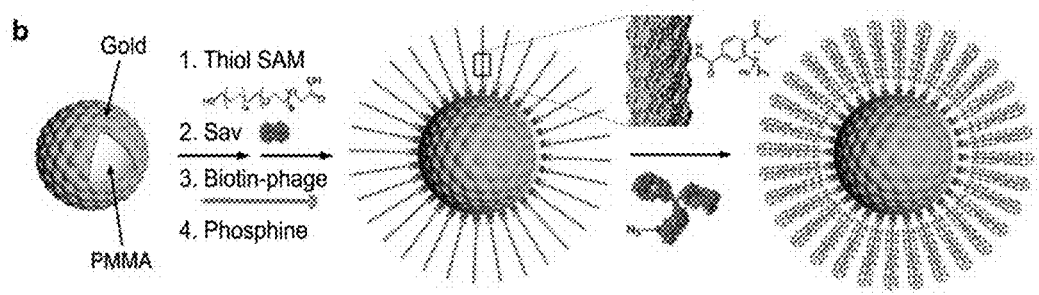

A virus-microbead complex capable of providing an increased surface area was prepared by binding of a linear virus to the microbead of the present invention, designed to exclude a non-specific binding in immunoassays and to provide an increased sensitivity, by controlling the orientation. In order for the virus to maintain its linear structure on the microbead intact, a conjuagation reaction with the microbead must lack intramolecular- and intermolecular-crosslinkings of the virus, while it must not interfere with the direct binding of the tip of virion to the microbead. Accordingly, the inventors of the present invention selectively biotinylated pIII to fix the regulated-orientation of fd virions, and used Staudinger ligation, a bioorthogonal and chemoselective cross linking between azide and phosphine, to ligate an antibody to the phage virions (FIG. 2).

7.1. Surface Modification of the Gold Microbead

First, in order to exclude a non-specific binding and to facilitate the binding of the virus, the surface of the gold microbead was modified with a SAM containing PEG, and then SAV, a protein that specifically binds to biotin, was introduced thereto. Specifically, 1 mg of gold microbead was subjected to rotary incubation with 0.5 ml of ethanol containing carboxyl-terminated hexa(ethylene glycol)undecane thiol (1 mM) at 25° C. for 16 hours. The gold microbead (5 µg), which was modified with SAM at 25° C. for 30 minutes, was added with 0.5 ml of MES buffer solution having a pH of 5.0 containing EDC (2 mM) and NHS (5 mM). The bead was then washed with 1 ml of PBS (pH 7.4) three times, and added with dissolved SAV (0.5 mg) in PBS (50 ul). The SAV-modified microbead was treated with PBS-PT (1% BSA, PBS containing 0.1% tween-20, pH 7.4) for 30 minutes, and the SAV loading was confirmed using biotin-alexa fluor 594.

Figure 3:
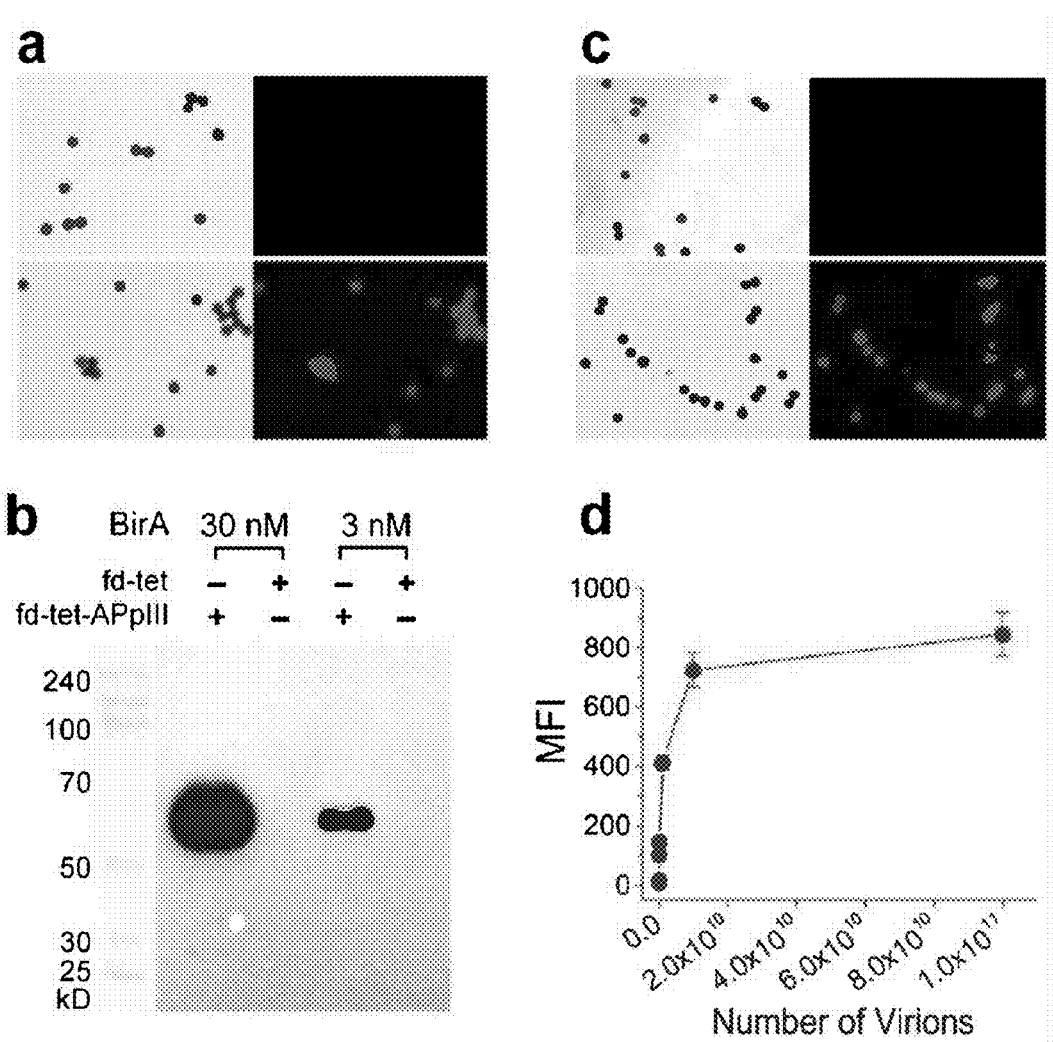
FIG. 3 shows an optimization of the surface modification of the gold microbead modified with SAV and phage virions according to the present invention. (a) is an optic and fluorescence microscopic image observed when the gold microbead introduced with SAV-SAM is pre-treated only with free biotin (top) or buffer solution (bottom), followed by visualizing with alexa fluor 594-biotin. (b) is an image of western blot analysis for treating a wild-type fd-tet and AP-tag fd-tet-APpIII virions ($10^{13}$) with BirA prior to visualizing with SAV-HRP. (c) is an optic and fluorescence microscopic image showing the detection of the BirA-treated fd-tet (top) and fd-tet-APpIII (bottom) phage virions ($1.0 \times 10^{10}$) bound to SAV-SAM gold microbead using a rabbit anti-fd antibody and an anti-rabbit alexa fluor 610-R-PE antibody. In (a) and (c), the left panel shows a bright-field light image and the right panel shows a fluorescence image. (d) shows titrations of virus loading using various amounts of biotinylated phage virions prepared in (b) under the same reaction conditions as in (c).

The result is shown in FIG. 3a. When the beads modified with SAM and SAV were pre-treated with five biotin, no fluorescence signal was observed even after the incubation with fluorescence-labeled biotin. On the other hand, when the bead was directly incubated with fluorescence-labeled biotin, a strong fluorescence signal was observed.

7.2. Optimization of a Phage Loading on the Gold Microbead

The biotinylated phage virions of a certain concentration range were rotary incubated with the SAV-modified gold microbead (5 µg), which was dissolved in PBS-BP (50 µl), at 25° C. for 16 hours. For a negative control group, wild-type fd-tet virions were used. The bead were washed with PBS three times and treated with an anti-fd rabbit IgG (37 ng) dissolved in PBS (50 µl) for 25° C. for 1 hour. After washing, the virions were incubated with an anti-rabbit alexa fluor 610-R-PE antibody (100 ng) dissolved in PBS (50 µl) for 25° C. for 1 hour to visualize the loading of phage virions, and the visualization was monitored by a fluorescence microscope.

For the site-specific biotinylation of the phage virions, a 14-mer bacterial biotin acceptor peptide (AP) having an amino acid sequence of GLNDIFEAQKIEWHE (SEQ ID NO: 3) was introduced into the front of pIII, which corresponds to the tail of fd-tet bacteriophage carrying a tetracycline-resistance determinant. The ε-amino group on Lys, a site for the specific biotinlyation located within an AP tag, is susceptible to chemical modifications to be followed by NHS for Staudinger ligation, and thus the inventors of the present invention have strived to in vivo biotinylate the phage with an endogenous biotin ligase BirA recognizing AP in bacteria cells. However the degree of in vivo biotinylation was insignificant, thus, in vitro biotinylation was performed by purifying BirA. When the AP including the phage (fd-tet-APpIII) was incubated with BirA, a clear band (~60 kD) was observed in western blot performed using a SAV (SAV-HRP) bound with horseradish peroxidase (HRP) (FIG. 3b). Then, the loading of virions on the SAV-gold microbead was confirmed, and the saturation of fluorescence was also confirmed when $1.0 \times 10^{19}$ virions and 5 µg of SAV-gold micobead were used (FIG. 3c). A single virion may be settled on the surface having an area from about $8.5 \times 10^{-17}$ to $1.4 \times 10^{-16}$ m$^2$ when the apparent diameter of N1-N1 terminal domain of pIII is 6 nm and the tail portion of fd virus is composed of 3 to 5 copies of pIII. Herein, 5 µg of gold microbead corresponds to 1000 beads, and thus the total surface area of the beads is about $7 \times 10^{-7}$ m$^2$, which corresponds to the theoretical value that can accommodate about 5 to $8 \times 10^9$ virions without a gap. When the virions were loaded on the actual microbead, the intensity of fluorescence reached near the theoretical value at $1.0 \times 10^{10}$ virions and remained constant throughout (FIG. 3d). Accordingly, $1.0 \times 10^{10}$ virions were used to maximize the loading of antibodies for further immunoassays while maintaining the efficiency in the phage preparation.

Figure 4:
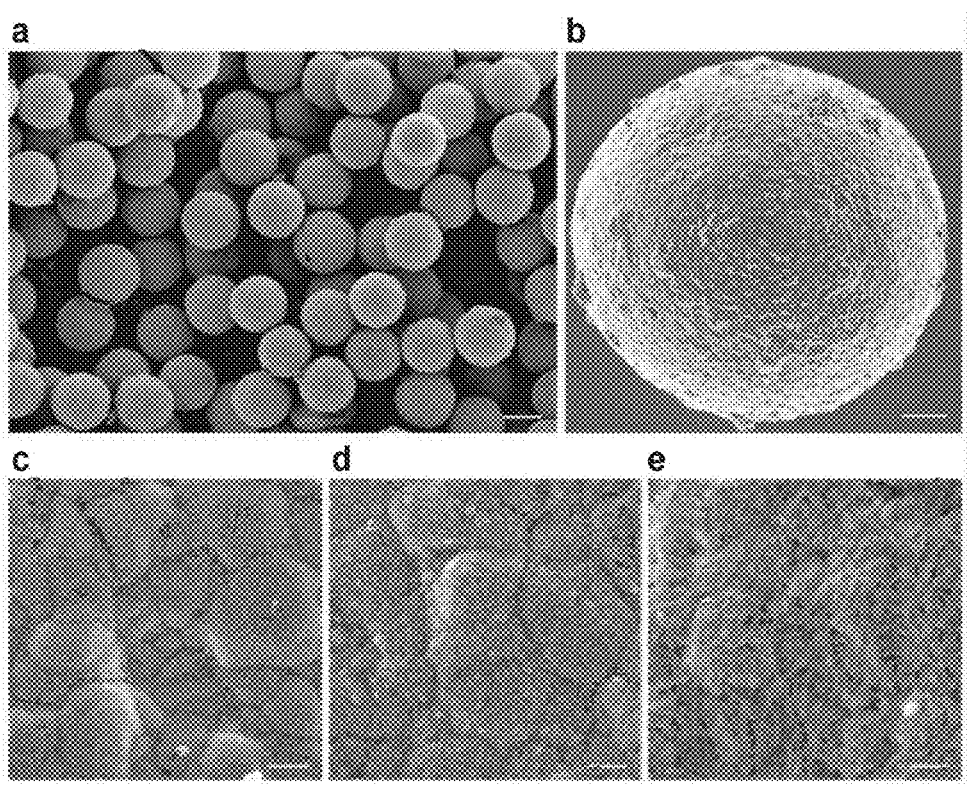
FIG. 4 shows SEM images of the microbead according to the present invention. (a) is a SEM image of the magnetic gold microbead (scale bar=10 μm). (b) is an enlarged image of the gold microbead showing the shape of the gold layer (scale bar=2 μm). (c) to (e) show images of a carboxyl-terminated hexa(ethylene glycol)undecane thiol SAM-modified bead, an image of a bead further bound with SAV, and finally an image of a Pt-sputtered surface of the bead bound with pIII biotinylated fd-tet phage virions, respectively (scale bar=100 nm).
Figure 5:
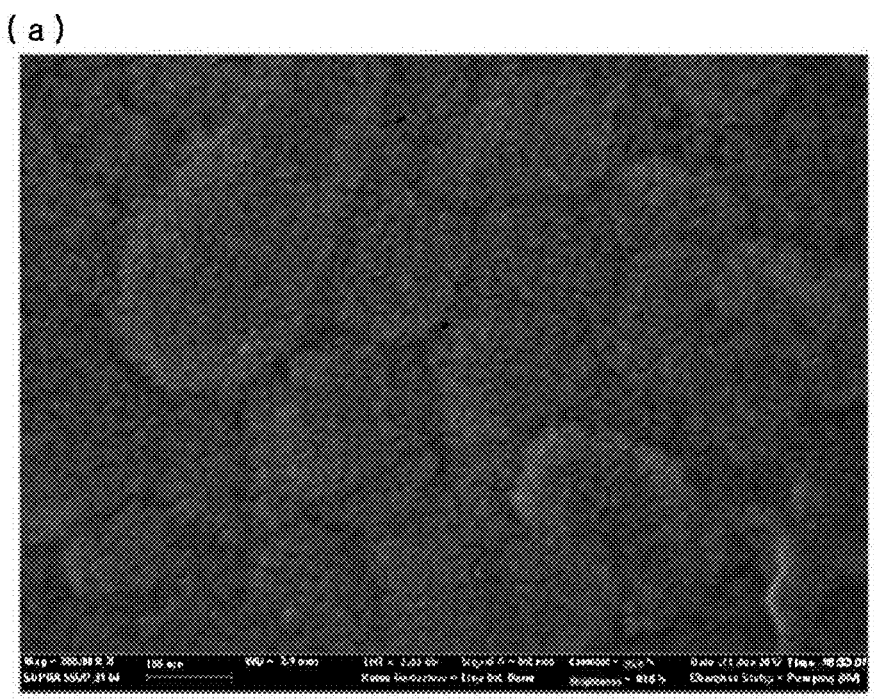
FIG. 5 shows SEM images illustrating a Pt-sputtered individual area of the SAV-modified gold microbead according to the present invention.
Figure 5:
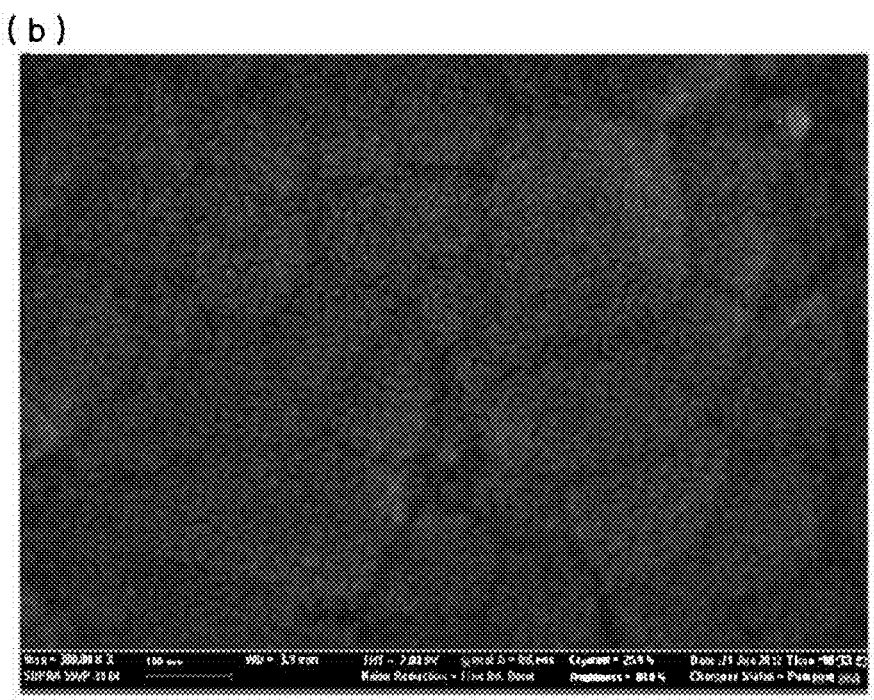
Figure 6:
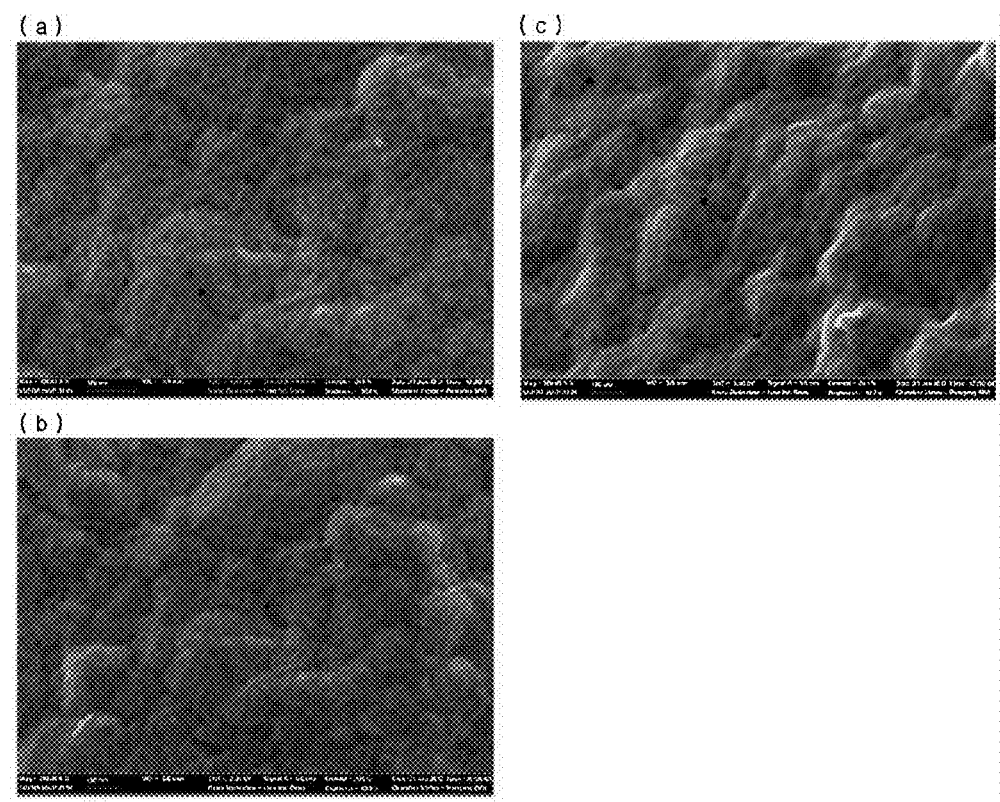
FIG. 6 shows SEM images illustrating a Pt-sputtered individual area having a different magnification of the SAV-gold-microbead treated with phage virions according to the present invention.

Next, the surfaces of gold microbead before and after the phage fixation were compared. 4(a) and 4(b) are FE-SEM images of a non-modified gold microbead exposing a layer of gold granules on the surface of the microbead. Even after the formation of thiol SAM, the surface of the bead the overall roughness similar to that of the non-modified gold microbead (FIG. 4c). In contrast, the SAV-modified surface showed a small pimple which is considered to be a Pt-coated SAV added onto the block of gold granules (FIGS. 4d and 5). Further, in case of the virus-modified surface, the virion fibers on the SAV layer having a 10 to 15 nm increased thickness were clearly identified due to sputtered platinum (FIGS. 4e and 6). The virion strand was found to be lying on the bead surface due to Pt sputtering required for a dry condition and FE-SEM operation.

7.3. Optimization of Staudinger Ligation

The SAV-modified bead (5 µg) was incubated with 0.5 ml of PBS solution, in which various concentrations of sulfo-NHS-phosphine were dissolved, at 25° C. for 1 hour, and was used as a positive control group. For preparing a viru-fixed bead, the SAV-modified bead was further incubated with 50 µl of PBS-BT containing $1 \times 10^{10}$ biotinylated phages at 25° C. for 16 hours, washed with PBS-BT and PBS three times, respectively, and incubated with 0.5 ml of PBS containing various amounts of sulfo-NHS-phosphine at 25° C. for 1 hour. For the Staudinger ligation, a mouse-derived primary antibody (100 µg) was incubated with NHS-PEG12-azide (0.1 and 1.0 mM) dissolved in PBS (0.1 ml) at 25° C. for 1 hour, and a dialysis was performed overnight. Phosphine-treated SAV- and virus-gold microbeads (5 µg) were incubated with an azide-modified mouse antibody (0.5 µg) dissolved in PBS at at 37° C. for 4 hour. The thus-obtained bead was washed with PBS-BT three times and incubated with the anti-mouse alexa fluor 594 antibody for a fluorescence microscope analysis. For a negative control group, an anti-mouse fluor 594 antibody directly treated with SAV- and virus-beads without the azide-modified antibody was used, and the background signal was excluded when detected.

Figure 7:
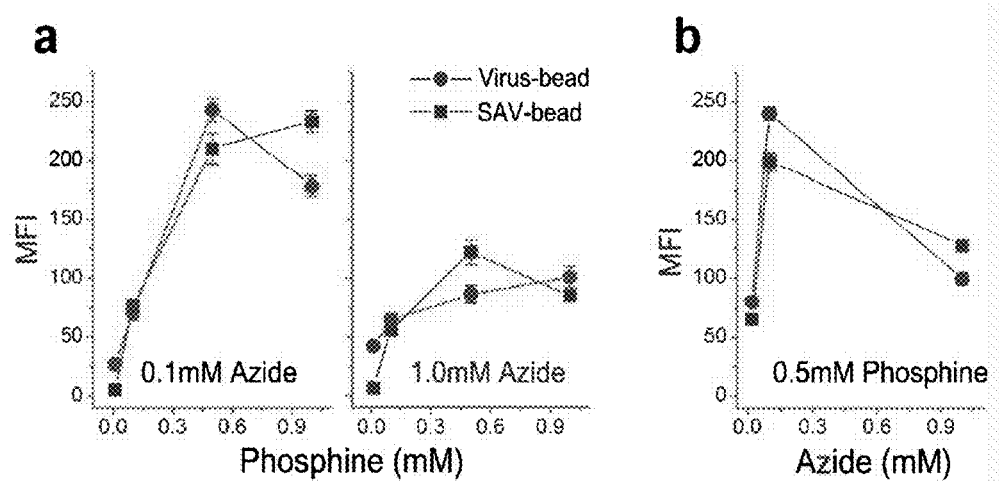
FIG. 7 shows an optimization process of a mouse antibody using Staudinger ligation. (a) shows observation results of the binding of the sulfo-NHS-phosphine treated SAV of 4 different concentrations or gold microbeads coated with phage virions to the mouse antibody incubated with 0.1 mM and 1.0 mM NHS-PEG$_{12}$-azide, respectively. (b) shows observation results of the gold microbeads modified with SAV or phage incubated with phosphine at a fixed concentration (0.5 mM) by changing the concentration of azide. An anti-mouse alexa fluor 594 was employed to measure mean fluorescence intensity (MFI).

The search process of optimization conditions for a specific antibody binding reaction is as follows. First, an amine-reactive NHS-PEG$_{12}$-azide labeled or sulfo-NHS-phosphine labeled antibody was optimized. Under the experimental conditions according to the present invention, the antibody was precipitated after incubating with sulfo-NHS-phosphine due to increased hydrophobicity of a branch resulted from a phenyl group on the phosphine. On the other hand, no precipitation was observed when the antibody was incubated with NHS-PEG$_{12}$-azide, and no visible changes in the SAV- and virus-beads were observed after labeling with sulfo-NHS-phosphine. That is, the SAV was fixed onto the microbead in advance to block further aggregation, and that the phages exhibit sufficient surface charges to neutralize the increased hydrophobic effect. After the binding of the azide-modified primary antibody to the phosphine-modified bead, the bead was stained with a fluorescence-labeled secondary antibody to measure the fluorescence intensity. The results are shown in FIG. 7. The strongest fluorescence intensity was observed when phosphine having an optimal concentration about 0.5 mM was reacted with 100 µM of azide (FIG. 7a). The antibody loading efficiency tended to decrease as a higher concentration (1.0 mM) of azide was used because an antigen-determining region of the primary antibody was buried inside blocking the access of the second antibody. Meanwhile, it was confirmed that the Staudinger ligation was not effective with a lower concentration of azide (20 μM) (FIG. 7b). However, the possibility of exhibiting a better antibody activity by a relatively low level of azide modification cannot be ruled out.

<Example 8> Cardiovascular Marker Assays

First, the SAV- and virus-gold microbeads (5 μg) were treated with PBS solution (0.5 ml) of sulfo-NHS-phosphine (0.5 mM) at 25° C. for 1 hour, and ligated with a rabbit polyclonal anti-cTnI capture antibody incubated with PBS solution (50 μl) of NHS-PEG12-azide (100 μM) at 37° C. for 4 hours. The thus-obtained bead was washed with PBS-BT three times and mixed with cTnI (0.02, 0.2, 2, and 10 ng/ml) or 0.5 ml of myoglobin (0.02, 0.2, 2, 10, 40, and 100 ng/ml) dissolved in PBS at 25° C. for 1 hour. For detecting cTnI in human serum, PBS was replaced with cTnI-spiked human serum (0.02, 0.2, 2, and 10 ng/ml, 0.5 ml). The bead was washed, incubated with an mouse monoclonal anti-cTnI detection antibody [19C7] dissolved in PBS at 25° C. for 1 hour, and visualized with the anti-mouse alexa fluor 594 antibody (500 ng). An analysis was performed without a marker protein under the same conditions to determine a background signal.

Figure 8:
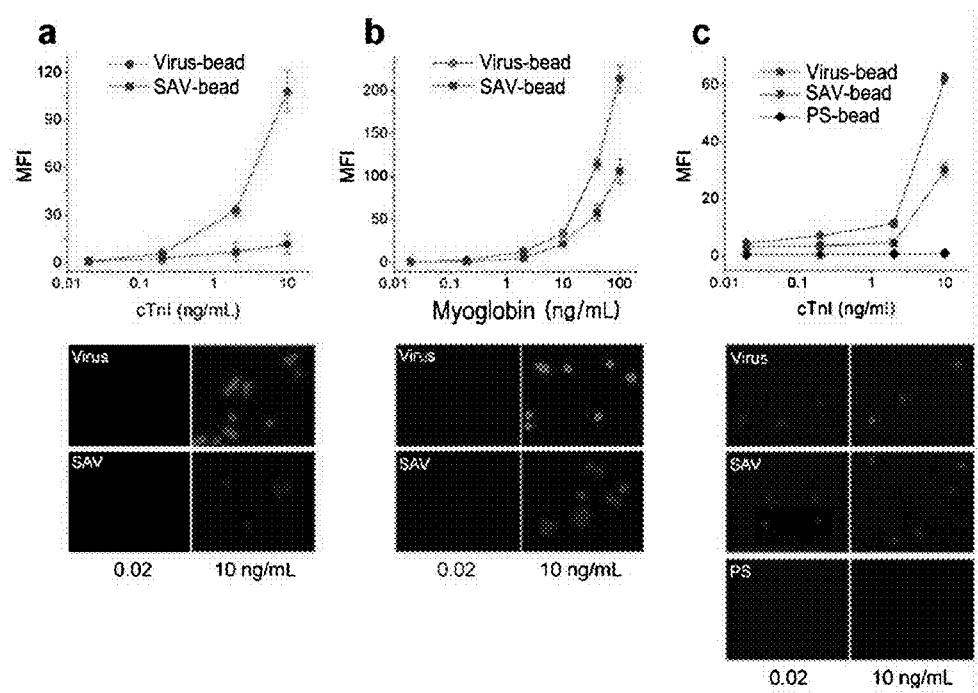
FIG. 8 shows sandwich immunoassay profiles (top) of a cardiovascular marker protein and representative fluorescence images (bottom) of the functionalized microbeads corresponding to the initial and final concentrations, respectively. (a) to (c) show the results of detecting PBS solution of cTnI having a certain concentration range, PBS solution of myoglobin, and serum containing cTnI using the virus- and SAV-gold-microbeads (a and b), and polymer microbeads (c), respectively.

Specifically, a biomimetic virus-microbead complex was compared with the SAV-coated bead in terms of an antibody activity against cTnI, a cardiovascular market protein, and myoglobin after loading of the antibody to confirm the effect of a long virus strand. The comparison was focused on the concentrations of a low range of cTnI and a relatively high range of myoglobin based on clinical applications. In an immunoassay using cTnI- and myoglobin-spiked PBS, the virus-modified gold microbead exhibited significantly improved signal compared to the SAV-modified gold microbead (FIGS. 8a and 8b). Concentrations of cTnI and myoglobin as low as 0.2 ng/ml were detected using the virus-microbead complex according to the present invention. The signal caused by the SAV-bead maintained at the level of background signal until the concentrations of cTnI and myoglobin reached 2.0 ng/ml. The effect of virions was rapidly increased at the higher concentration of cTnI, increasing the fluorescence signal up to 9-fold at a concentration of 10 ng/ml compared to the SAV-bead, whereas a two-fold increase was observed at the concentration range of ≤100 ng/ml of myoglobin. Also, the difference in the increase was resulted from the intrinsic factors of antigen such as a size, structure, and coupling constant of the primary antibody, etc. It is necessary to be worth noting that the difference observed in an analysis performing ability is greater than the difference observed in the loading of antibodies between SAV- and virus-beads (FIGS. 7 and 8). Further, the effect of the virus fibers was prominent in the antibody detection performed by a sandwich analysis, when the amount of captured antigens was limited. Accordingly, the improved sensitivity in the immunoassay using the virus-microbead complex is attributed to the characteristics of a long, flexible virus filament that considerably increases acceptability of analyte-capturing-antibody and receptor-ligand interaction.

Figure 9:
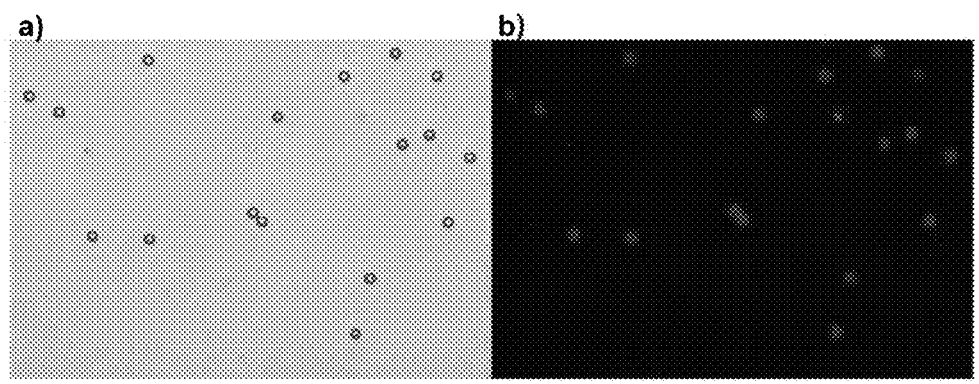
FIG. 9 shows immunoassay results using the virus-microbead complex according to the present invention. It illustrates the immunoassay results of cTnI (10 ng/ml) dissolved in PBS using polystyrene beads having a diameter of 10 μm, in which the surface is modified with anti-cTnI via EDC/NHS chemistry. (a) and (b) show a differential interference contrast (DIC) image and a fluorescence image, respectively.

The preventive role of a SAM-gold film against a non-specific adsorption is prominent in an immunoassay using serum analyte containing cTnI. Both the virus- and SAV-beads were able to detect up to 20 pg/ml of cTnI (FIG. 8c). Meanwhile, the SAV-bead showed a partial improvement at a high concentration of cTnI (10 ng/ml) having a sensitivity equal to half of the virus-bead. Specifically, a concentration-dependent fluorescence signal was observed in cTnI range of low concentrations in case of the virus-bead alone. On the other hand, although a typical carboxylated polystyrene (PS) bead bound with an antibody on the surface by EDC-NHS chemistry was able to detect cTnI in PBS (FIG. 9), the polymer bead was not able to produce a signal within the scope of the present invention in serum. From the result, it was confirmed that the antibody and SAM-gold protective layer densely bound to the phage tentacle improved the sensitivity against a marker protein of a low range by a synergistic effect, however, the reason for increasing the sensitivity against cTnI in serum is unclear.

What is claimed is:

1. A virus-microbead complex comprising:
   (i) a microbead made of gold or coated with a thin gold film,
   (ii) a self-assembled monolayer (SAM) on the surface of the microbead, which is composed of carboxyl-terminated hexa(ethylene glycol)undecane thiol bound to streptavidin or biotin, preventing non-specific binding on the surface of the microbead,
   (iii) a virus layer having one end of each linear virus bound to the SAM on the surface of the microbead,
   wherein the individual linear virus in the virus layer are independently bound to the SAM, and
   wherein the binding between the SAM on the surface of the microbead and the linear viruses is mediated by the binding between streptavidin (SAV) and biotin to separate one linear virus to another linear virus in the virus layer.

2. The complex of claim 1, wherein at least two capturers capable of capturing an analyte are bound to the exposed long axis surface of the virus in the virus layer.

3. The complex of claim 2, wherein the capturer is selected from the group consisting of an antibody, an antigen, a ligand, and a receptor.

4. The complex of claim 1, wherein the linear virus is filamentous bacteriophage fd phage or M13 phage.

5. The complex of claim 1, wherein biotin or streptavidin is bound to a protein located at one end of the virus, or the virus is gene-manipulated to express a fusion protein of biotin or streptavidin and a virus protein.

6. The complex of claim 5, wherein the protein located at one end of the virus is pIII, pVI, pVII, pIX, or a combination thereof.

7. The complex of claim 1, wherein the microbead is magnetic.

8. An immunoassay kit comprising the virus-microbead complex of claim 1.

9. The kit of claim 8, comprising the complex; and further a capturer for capturing an analyte, which is bindable to the surface of the virus within the complex.

10. The kit of claim 8, wherein the virus and the capturer for capturing an analyte are linked by a covalent bond.

11. The kit of claim 10, wherein the covalent bond is achieved by Staudinger ligation.

12. The kit of claim 8, wherein the kit is for suspension array.

13. The kit of claim 8, wherein when the microbead is magnetic, the kit can separate an analyte by separating the complex bound to the analyte using a magnetic property.

14. The complex of claim 3, wherein the antibody is modified with azide, and linked to the phosphine group bound to Ala or Lys residue located at N-terminal of the coat protein exposed to the surface of the linear virus.

* * * * *